United States Patent [19]

Smith

[11] Patent Number: 5,385,140

[45] Date of Patent: Jan. 31, 1995

[54] AEROSOL INHALATION DEVICE

[75] Inventor: Collin M. Smith, New South Wales, Australia

[73] Assignee: Lindrew Pty Limited, Hamilton, Australia

[21] Appl. No.: 132,226

[22] Filed: Oct. 6, 1993

Related U.S. Application Data

[63] Continuation of Ser. No. 882,342, May 13, 1992, abandoned.

[30] Foreign Application Priority Data

May 14, 1991 [AU] Australia ............... PK6139

[51] Int. Cl.⁶ ............................................. A61M 11/00
[52] U.S. Cl. ........................... 128/200.23; 128/203.23; 128/203.24; 128/203.29; 137/512.4
[58] Field of Search ................ 128/200.14, 200.23, 128/200.24, 203.12, 203.23, 203.24, 203.29, 206.21, 205.24, 207.12, 207.16, 201.28; 137/512.4

[56] References Cited

U.S. PATENT DOCUMENTS

| | | | |
|---|---|---|---|
| 3,527,242 | 9/1970 | Ansite | 137/512.4 |
| 3,547,561 | 12/1970 | Lavon | 137/512.4 X |
| 4,259,951 | 4/1981 | Chernack et al. | 128/200.14 |
| 4,437,490 | 3/1984 | Demers et al. | 137/512.4 |
| 4,534,343 | 8/1985 | Nowacki | 128/200.23 |
| 4,708,606 | 11/1987 | Zambelli | 417/559 |
| 4,953,584 | 9/1990 | Vegso | 137/218 |
| 4,954,252 | 9/1990 | Griffin | 210/136 |
| 5,012,803 | 5/1991 | Foley | 128/200.23 |
| 5,012,804 | 5/1991 | Foley | 128/200.23 |
| 5,042,467 | 8/1991 | Foley | 128/200.23 |
| 5,074,294 | 12/1991 | Chiesi | 128/200.14 |
| 5,134,993 | 8/1992 | Van Der Linden | 128/200.14 |

FOREIGN PATENT DOCUMENTS

| | | | |
|---|---|---|---|
| 270056 | 4/1969 | Austria | 128/200.14 |
| 678683 | 9/1952 | United Kingdom | 137/512.4 |
| 1544440 | 2/1990 | U.S.S.R. | 128/200.23 |
| 9210228 | 6/1992 | WIPO | 128/200.14 |

Primary Examiner—Edgar S. Burr
Assistant Examiner—Eric P. Raciti
Attorney, Agent, or Firm—Sterne, Kessler Goldstein & Fox

[57] ABSTRACT

A diaphragm valve mechanism comprises a diaphragm valve support structure having passages extending therethrough. Projecting normal to a grid are a number of locating pins which are adapted to extend through holes in the diaphragm valve. The diaphragm valve is formed of flexible material and is provided with a pair of cross slits, each corresponding with the grid bridge element. The central portion of the diaphragm valve is located within a major flow passage whereas the outer peripheral edge portion of the diaphragm valve is located within an exit passage.

9 Claims, 7 Drawing Sheets

AEROSOL INHALATION DEVICE

This application is a continuation of application Ser. No. 07/882,342, filed May 13, 1992, now abandoned.

FIELD OF THE INVENTION

The following invention relates to an aerosol inhalation device particularly useful for the inhalation of aerosol drug particles by an asthmatic.

PRIOR ART

Medication inhalers of the above type are known. Such inhalers comprise an elongated aerosol holding chamber, through a remote end from a user of which, aerosol drug particles are received. At an end of the chamber proximal to the user, a diaphragm valve is often provided. Such a valve is adapted to open as the user inhales so as to allow passage therethrough of the particulate medication from the chamber. Upon the user's exhaling, the diaphragm valve closes to prevent passage of breath therethrough back into the chamber. Several breaths are often required for administration of the required drug dosage. It is a disadvantage of such devices that it can be quite difficult for the user to exhale, as in order to establish proper operation of the diaphragm valve, it is necessary to substantially inhibit the flow of exhaled breath.

Furthermore, most known devices of this type have substantial flow passage "dead zones" which result in wasted medication and general inefficiency.

Other devices comprise spring loaded valve mechanisms which are cumbersome and expensive to manufacture.

OBJECT OF THE INVENTION

It is the object of the present invention to overcome or substantially ameliorate at least one of the above disadvantages.

DISCLOSURE OF THE INVENTION

There is disclosed herein in accordance with a first preferred form of the invention apparatus comprising:
- a housing adapted to cooperate with, attached to, or formed integrally with a chamber to define a major fluid passage comprising an upstream zone within the chamber and a downstream zone,
- a major fluid exit provided in the downstream zone,
- a back-flow fluid exit in selective fluid communication with the downstream zone, and
- a diaphragm mounted within the housing and comprising;
  - major valve means interfacing the upstream and downstream zones and being openable to allow fluid flow therethrough from the upstream zone to the downstream zone and through the major fluid exit, and
  - exit valve means across the back-flow fluid exit being closeable when the major valve means is opened and openable when the major valve means is closed and when fluid pressure in the downstream zone is higher than ambient pressure so as to allow escape of fluid from the downstream zone to atmosphere via the back-flow fluid exit.

There is further disclosed herein in accordance with a second preferred form of the invention a combination comprising the valve mechanism of the first preferred form and a chamber having formed thereon a grid extending across the major fluid passage adjacent to and supporting diaphragm, which grid comprises passages extending therethrough.

In accordance with a third preferred form of the invention, there is further disclosed herein an aerosol inhalation device comprising an aerosol holding chamber having disposed at one end thereof a diaphragm valve mechanism in accordance with the first preferred form mentioned above.

BRIEF DESCRIPTION OF THE DRAWINGS

A preferred form of the present invention will now be described by way of example with reference to the accompanying drawings, wherein.

DETAILED DESCRIPTION OF THE PREFERRED EMBODIMENT

Figure 2:
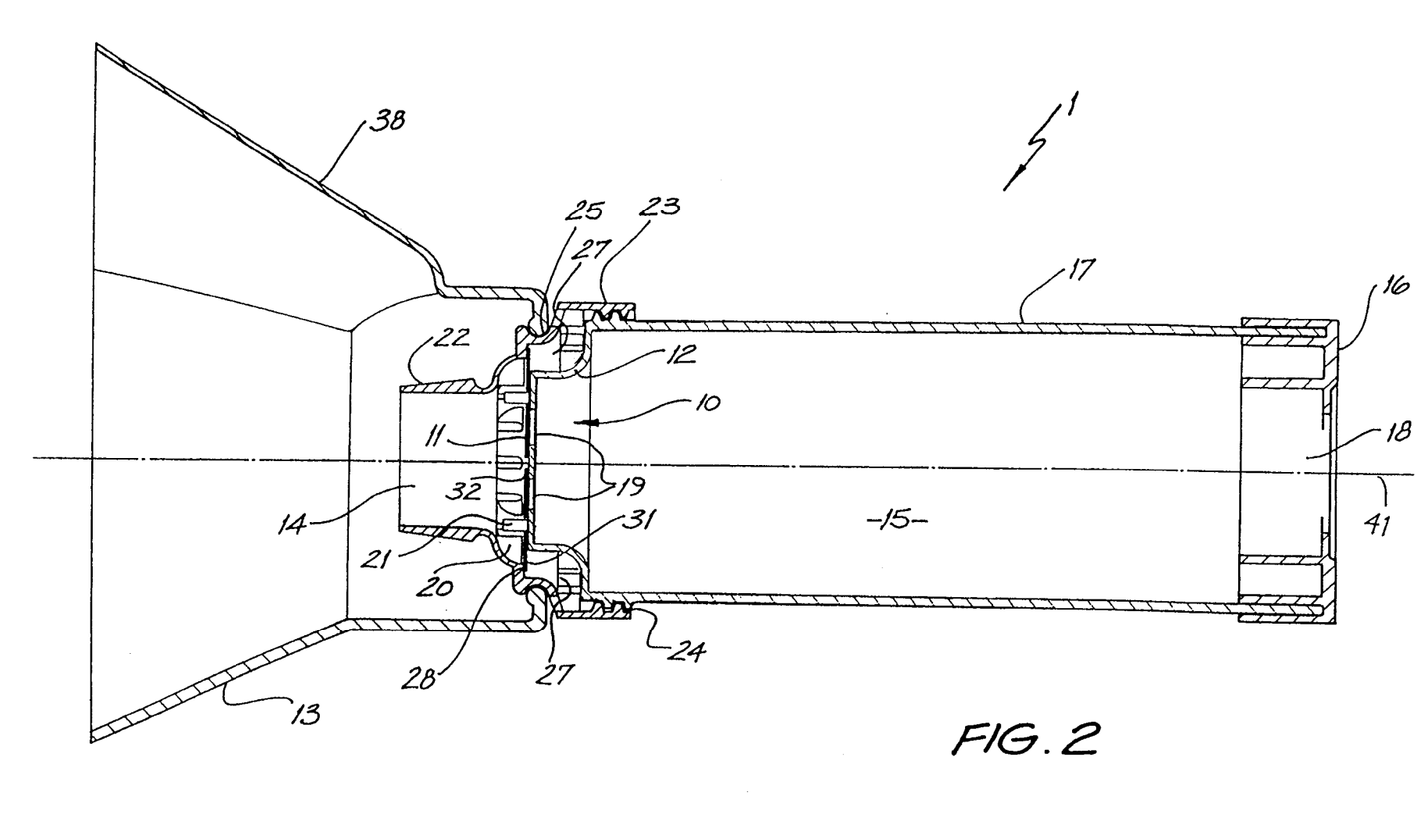
FIG. 2 is a schematic cross-sectional elevational view of an aerosol inhalation device comprising the diaphragm valve mechanism of FIG. 1.
Figure 7A:
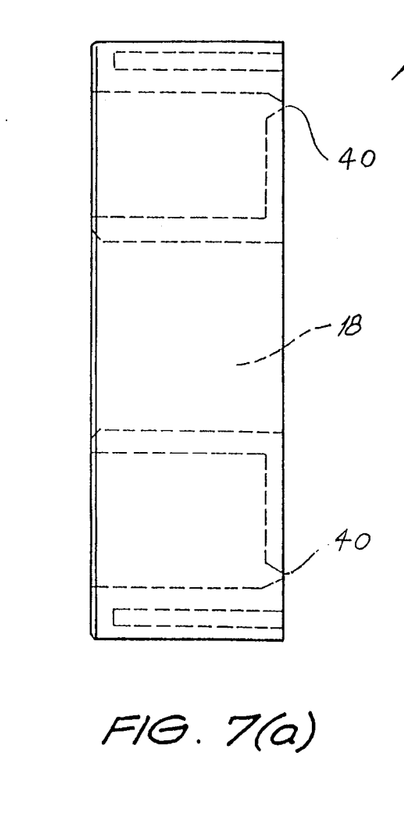
Figure 7B:
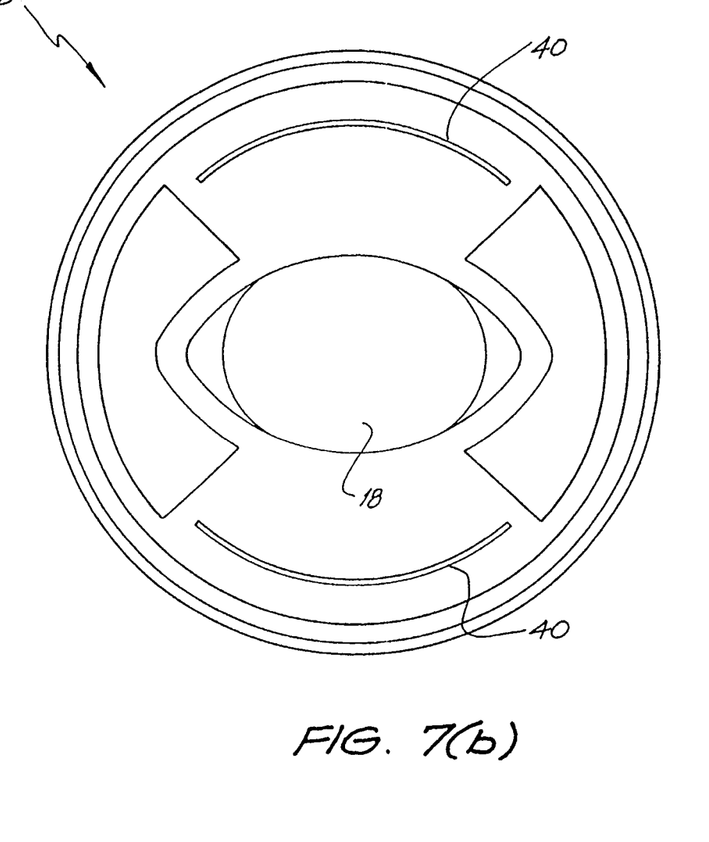

In the accompanying drawings there is schematically depicted an aerosol inhalation device 1. Device 1 comprises an aerosol holding chamber 15 having attached to one end thereof (the end distal of a user when in use) a flexible cap 16. Flexible cap 16 is adapted to fit over the distal end of cylindrical shell 17 and comprises an aperture 18 through which a standard inhaler mouthpiece is sealingly inserted so as to dispense airborne medication into chamber 15. Flexible cap 16 further comprises a number of valve slits 40 which open inwardly towards chamber 15 when fluid pressure therein is lower than ambient pressure. The tapered form of each valve slits 40 prevents opening thereof when fluid pressure within chamber 15 is higher than ambient pressure.

As an alternative to the provision of valve slit 40, any form of valve mechanism may be provided in cap 16.

Aerosol holding chamber 15 in the preferred embodiment comprises a cylindrical shell 17 having mounted thereto or formed integrally at the proximal end thereof, a housing 23 surrounding B diaphragm valve mechanism 10.

Figure 1:
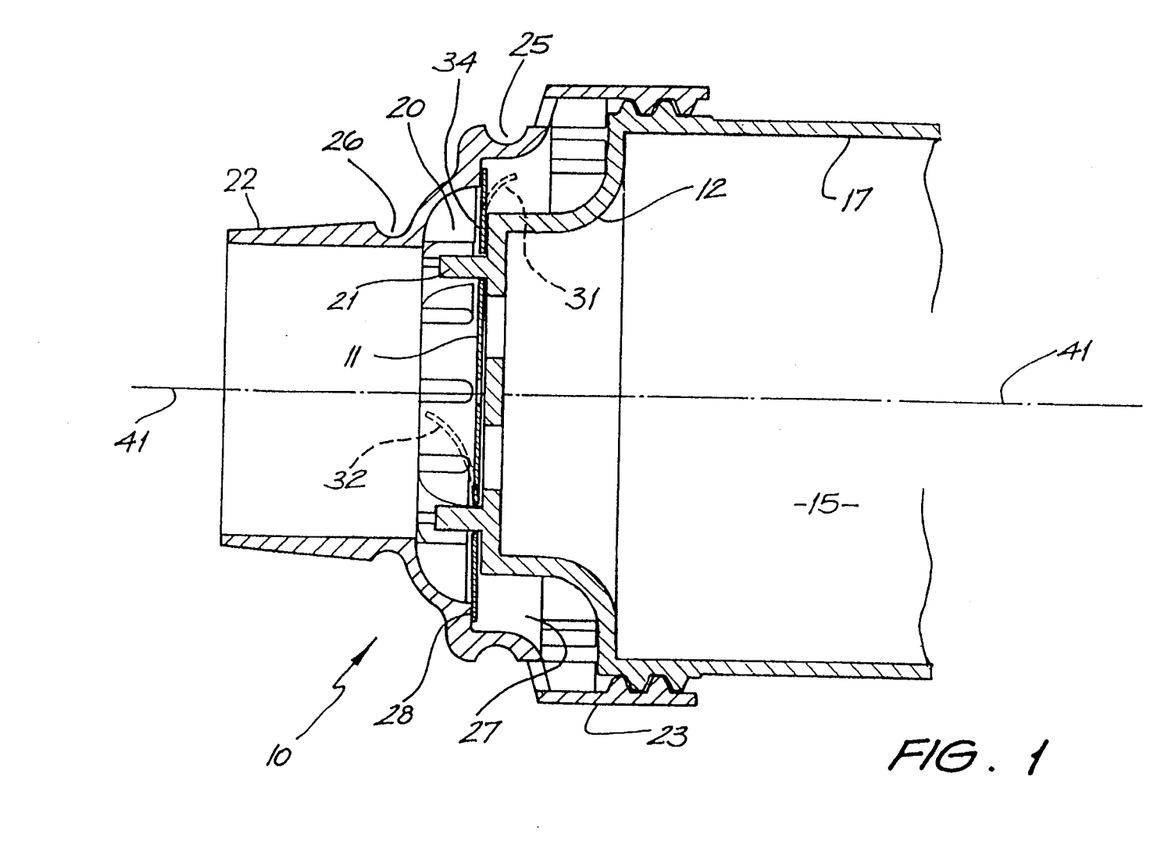
FIG. 1 is a schematic cross-sectional elevational view of a diaphragm valve mechanism showing the diaphragm valve in two operational positions.

Diaphragm valve mechanism 10 comprises a diaphragm valve 11 supported by a supporting structure 12. Cylindrical shell 17, housing 23 and diaphragm valve support structure 12 are typically formed of a moulded plastics material. Attached to housing 23 and as shown in FIGS. 1 and 2 via a large annular recess 25 is a face mask 13. Provision is made by way of a small annular recess 26 for fitting of a smaller child of infant sized face mask (not shown). Face mask 13 may be reversed and attached to annular recess 25 so as to locate mask 13 in a convenient storage position over and around cylindrical shell 17.

Face mask 13 is an optional feature as mouthpiece 22 is provided surrounding exit port 14 of housing 23.

Figure 3:
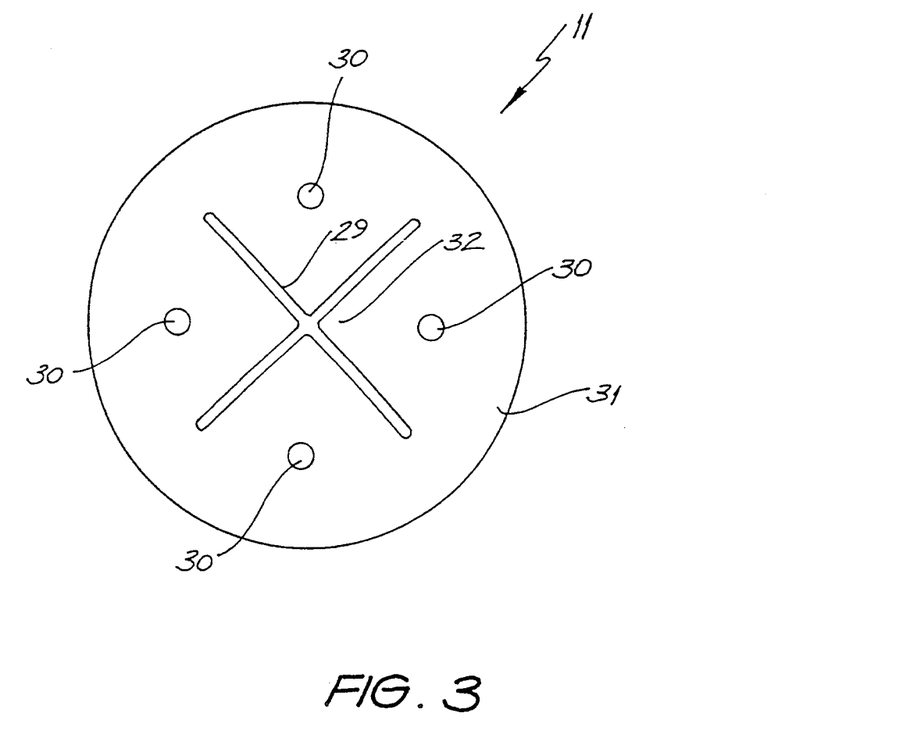
FIG. 3 is a schematic end elevational view of a diaphragm valve.
Figure 4A:
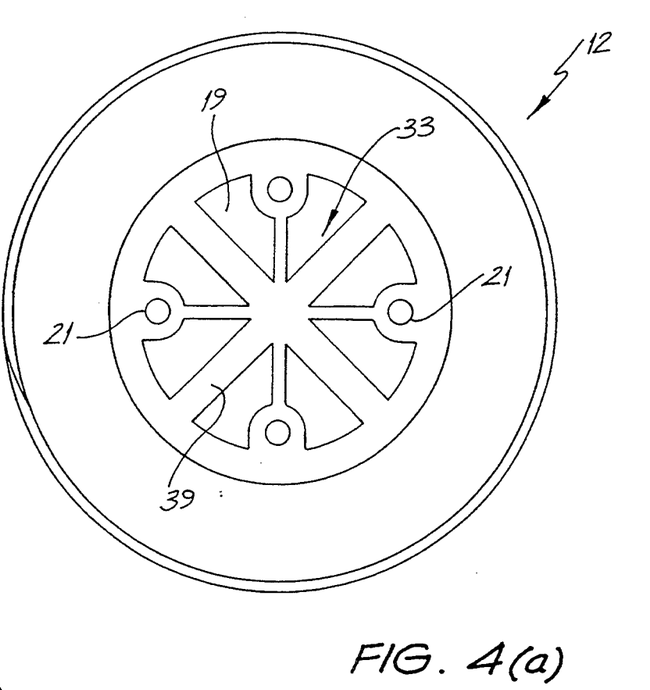
FIGS. 4(a) and 4(b) are schematic end elevational and side elevational views respectively of a diaphragm support structure forming part of the diaphragm valve mechanism depicted in FIG. 1, FIGS. 5(a) and 5(b) are schematic side elevational and end elevational views respectively of a housing forming part of the diaphragm valve mechanism depicted in FIG. 1, FIGS. 6(a) and 6(b) are schematic side elevational and end elevational views respectively of a mask adapted to be attached to the aerosol inhalation device depicted in FIG. 2, and FIGS. 7(a) and 7(b) are schematic side elevational and end elevational views respectively of a flexible end cap forming part of the aerosol inhalation device depicted in FIG. 2.
Figure 4B:
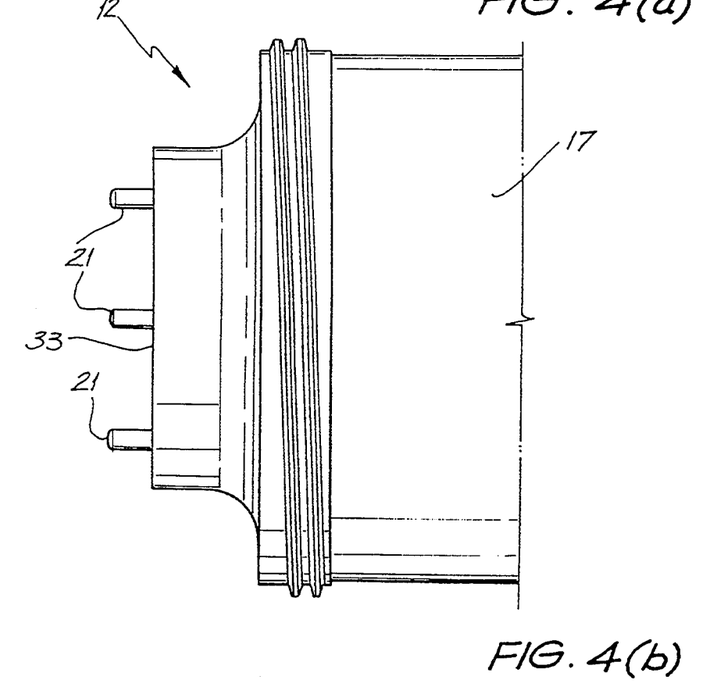

Turning particularly to FIG. 4(a), diaphragm valve support structure 12 is shown comprising a grid 33 having passages 19 extending therethrough. Projecting normal to grid 33 are four locating pins 21 which are adapted to extend through holes 30 as depicted in FIG. 3 through diaphragm valve 11.

Referring to FIG. 3, diaphragm valve 11 being formed of flexible material is provided with a pair of cross slits 29, each cross slit 29 corresponds with a grid bridge element 39.

Returning now to FIG. 1, which shows two separate operational positions of valve 11, each position being shown on opposite sides of centre line 41, diaphragm valve support structure 12 is positioned within housing 23 in lateral spaced relation thereto so as to provide an annular exit passage 27 therebetween. It should be appreciated that central portion 32 of diaphragm valve 11 is located within the major flow passage 19 whereas outer peripheral edge portion 31 of diaphragm valve 11 is located within exit passage 27.

So as to prevent diaphragm valve 11 from lifting away from grid 33, a plurality of positioning pins or projections 20 are moulded integrally with housing 23. Each positioning pin 20 is separated from diaphragm valve 11 by a thin gap 34. This gap should typically be as small as possible so as to prevent-movement of diaphragm valve 11 without actually asserting force thereto in a rest position. Such force might otherwise distort valve 11.

The outer periphery 31.of diaphragm valve 11 is adapted to rest against an annular sealing 1edge 28 of housing 23.

Figure 5A:
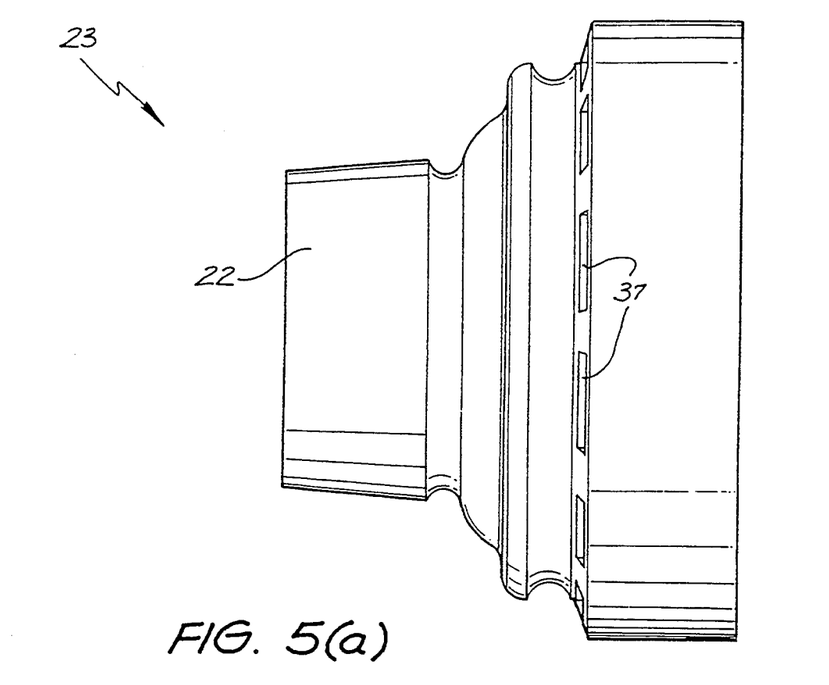

Housing 23 as best depicted in FIG. 5(a) shows a plurality of exit ports 37 spaced circumferentially therearound. Exit ports 37 are in fluid communication with exit passage 27 and allow exit of fluid from passage 27 to atmosphere.

Figure 5B:
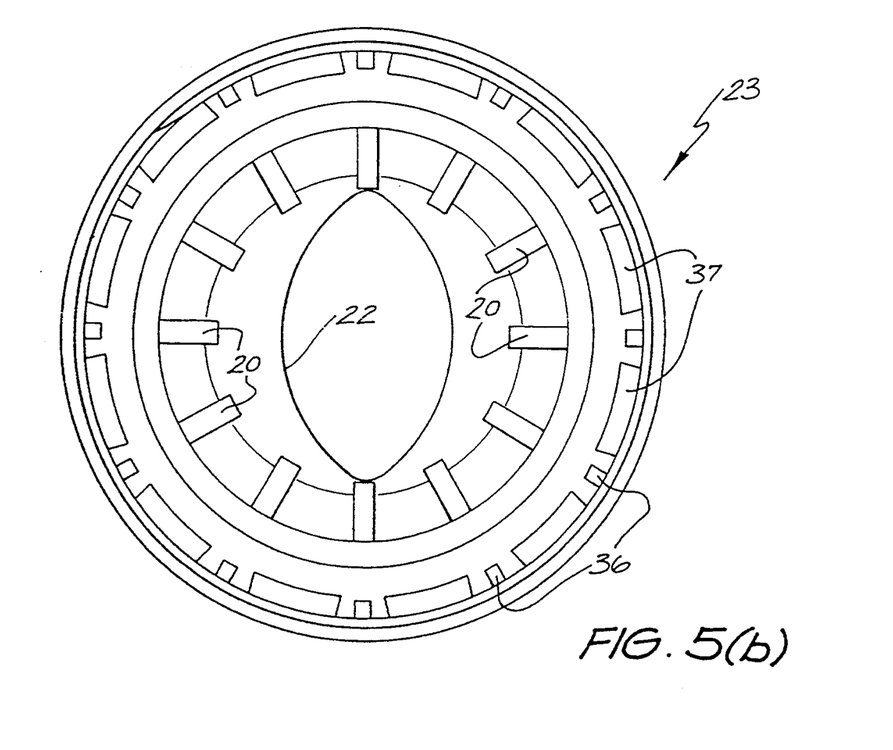

Depicted in FIG. 5(b) is a number of protrusions 36 which serve to aid in retaining housing 23 to cylindrical shell 17.

Figure 6A:
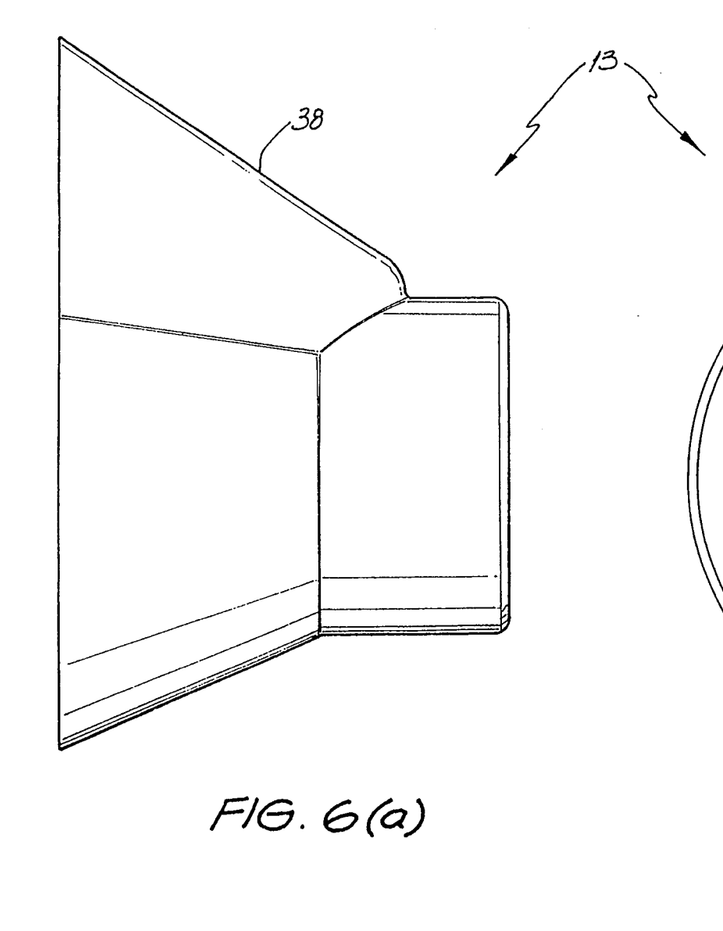
Figure 6B:
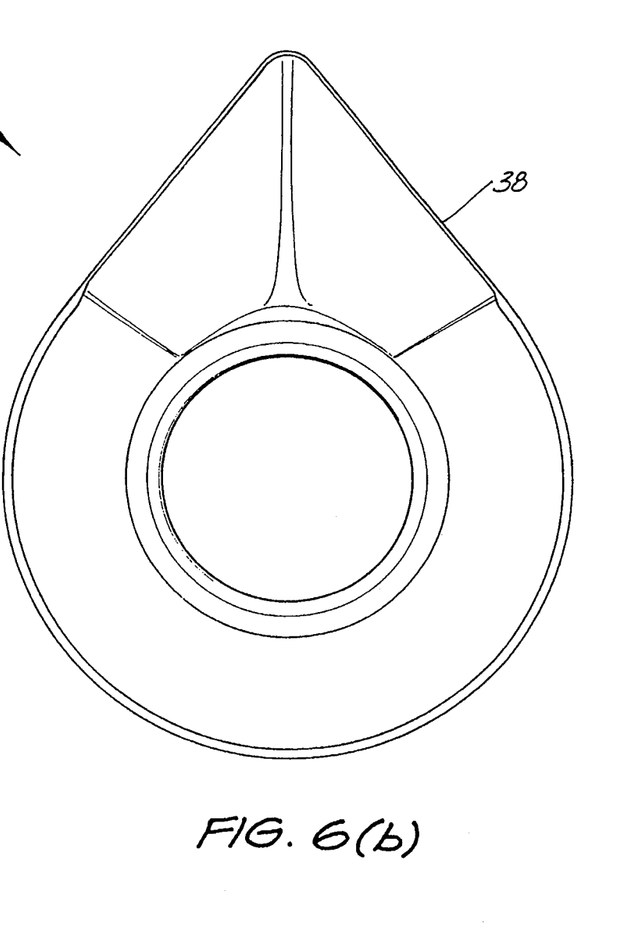

In use, a standard inhaler mouthpiece will be inserted through aperture 18 so as to provide aerosol to chamber 15. A user would have placed his or her mouth over mouthpiece 22 or alternatively, the mask 13 which comprises nose cover 38 may be utilised to establish a fluid seal between aerosol holding chamber 15 and the user.

Upon breathing inwardly, central portion 32 of diaphragm valve 11 will open whilst at the same time outer edge portion 31 of diaphragm valve 11 will close onto sealing ledge 28. Accordingly, aerosol suspended within chamber 15 will pass through the diaphragm valve 11 to be breathed in by the user.

Upon the user exhaling, central portion 32 will close and be retained in a closed position against grid 33 of diaphragm valve support structure 12. At the same time, peripheral outer edge portion 31 of diaphragm valve 11 will open-so as to allow the user's exhaled breath to escape via passage 27.and exit ports 37.

If necessary, several breaths may be taken wherein, the operation of diaphragm valve 11 repeats the above described steps.

During an inward breath, non-return valves 40 will open allowing air to enter chamber 15 thus displacing the suspended aerosol-therein. Upon an outward breath, non-return valves 40 will close so as to prevent any inadvertent escape of aerosol from chamber 15.

It should be appreciated that modifications and alterations obvious to those skilled in the art are not to be considered as beyond the scope of the present invention. For example, diaphragm valve support structure 12, rather than being glued or otherwise affixed to shell 17 may be moulded integrally therewith. Furthermore, the specific means of retaining diaphragm valve 11 to support structure 12 may be altered without departing from the scope of the invention.

In addition, a breathing indicator for example in the form of a thin section of mask 13 may be provided. As such, the thin section will protrude and retract to indicate breathing to a doctor for example.

The applicant also envisages that any suitable type of valve or valves may replace non-return valves 40.

I claim:

1. Apparatus comprising:

a housing adapted to cooperate with, attached to, or formed integrally with a chamber to define a major fluid passage comprising an upstream zone within the chamber and a downstream zone;

a major fluid exit provided in the downstream zone;

a back-flow fluid exit in selective fluid communication with the downstream zone, said back-flow fluid exit comprising an annular passage surrounding said major fluid passage, said annular passage comprising an annular sealing ledge; and a diaphragm, mounted within the housing, comprising:

a central region, comprising crossed slits defining a plurality of flaps interfacing the upstream and downstream zones and being operable to allow fluid flow therethrough from the upstream zone to the downstream zone and through the major fluid exit, and a continuous peripheral region across the back-flow fluid exit being closeable by resting against said annular sealing ledge when the major valve means is opened and operable upon deflection at the periphery away from said sealing ledge when the central region is closed and when fluid pressure in the downstream zone is higher than ambient pressure so as to allow escape of fluid from the downstream zone to atmosphere via the back-flow fluid exit.

2. In combination, the valve mechanism of claim 1 and a chamber having formed thereon a grid extending across the major fluid passage adjacent to and supporting the diaphragm, which grid comprises passages extending therethrough.

3. The combination of claim 2 further comprising a plurality of locating pins extending essentially normally from the grid, and wherein the diaphragm is provided with a plurality of apertures adapted to fit over said pins.

4. The valve mechanism of claim 1 wherein said central region comprises at least two slits providing at least one flap in said diaphragm.

5. In combination, the valve mechanism of claim 1 and a chamber having formed thereon a grid bridge extending across the major fluid passage adjacent to and supporting the diaphragm, and wherein the diaphragm comprises at least one slit providing at least one flap in said diaphragm and wherein said grid bridge comprises at least one grid corresponding in location to the location of said slit in said diaphragm.

6. The valve mechanism of claim 1 wherein the housing further comprises a plurality of positioning projections, each adapted to retain said diaphragm in position.

7. An aerosol inhalation device comprising an aerosol chamber having disposed at one end thereof the apparatus of claim 1.

8. The aerosol inhalation device of claim 7 further comprising a flexible cap adapted to fit over one end of the housing and comprising an aperture through which a standard inhaler mouthpiece is adapted to be sealingly inserted so as to dispense airborne medication into the chamber.

9. The aerosol inhalation device of claim 8 wherein said cap further comprises a valve or constriction adapted to separate the chamber from the exterior thereof so as to impair back-flow of fluid from within the chamber to atmosphere.

* * * * *